United States Patent [19]

Brent et al.

[11] Patent Number: 4,833,080

[45] Date of Patent: May 23, 1989

[54] REGULATION OF EUCARYOTIC GENE EXPRESSION

[75] Inventors: Roger Brent; Mark S. Ptashne, both of Cambridge, Mass.

[73] Assignee: President and Fellows of Harvard College, Cambridge, Mass.

[21] Appl. No.: 808,166

[22] Filed: Dec. 12, 1985

[51] Int. Cl.$^4$ .................. C12N 15/00; C12N 21/00; C12N 7/00; C12P 19/34

[52] U.S. Cl. .................. 435/172.3; 438/68; 438/91; 438/235; 438/317.1; 438/320; 438/255; 536/27; 931/29; 931/32; 931/33; 931/34; 931/56; 931/69

[58] Field of Search .................. 435/68, 70, 71, 172.3, 435/317, 317.1, 320; 935/28, 40, 56, 69, 32-34; 536/27

[56] References Cited

PUBLICATIONS

Wharton et al., (1984) Cell 38: 361-369.
Echols pp. 252-262 in The Bacteriophage Lambda, ed. Hershey, Cold Spring Harbor Labs, New York, 1971.
Guarente et al. (1982) PNAS 79: 1410.
Sinclair et al., J. Mol. Cell. Biol., vol. 5, p. 3208 (1985).
Guarente et al., Cell, vol. 36, p. 799 (1984).
Guarente et al., Proc. Natl. Acad. Sci. U.S., vol. 79, p. 7410 (1982).
West et al., Molec. Cell Biol., vol. 4, p. 2467 (1984).
Brent et al., Nature, vol. 312, pp. 612-615 (1984).
Brent et al., Cell, vol. 43(2), pp. 729-736 (Dec. 1985).

Primary Examiner—Thomas G. Wiseman
Assistant Examiner—S. Seidman

[57] ABSTRACT

Regulation of eucaryotic gene expression is controlled by procaryotic peptides. The peptides recognize specific DNA sequences present in the gene, which may be derived from procaryotic genes, and either activate or repress gene transcription. Hybrid procaryotic peptides may be used containing both repressor and activator peptides.

32 Claims, 4 Drawing Sheets

REGULATION OF EUCARYOTIC GENE EXPRESSION

BACKGROUND OF THE INVENTION

This invention relates to the regulation of eucaryotic gene expression by procaryotic proteins.

Commercial production of eucaryotic proteins may involve the in vivo expression of cloned genes. Such cloned genes may be expressed in either procaryotic or eucaryotic systems. Some proteins, for example, Tissue Plasminogen Activator factor, are best synthesized in a eucaryotic cell since the protein must be correctly folded to be functional and for some proteins this process cannot, as yet, be performed by procaryotic cells. Some cell lines which have cloned genes to produce proteins, for example, those that produce Colony Stimulating Factor, are unstable possibly because the protein produced is deleterious to the cells producing it. In procaryotes such problems are overcome by expressing the cloned gene from a regulated promoter. For example, by altering environmental conditions the promoter can be used to reduce gene expression during cell growth and then to increase expression when required. Although the cells may die when gene expression is turned on, the protein is produced and the cells can be readily replenished. In eucaryotic cells some promoters have been characterized which also regulate gene expression, for example, the promoter of the metallothionine gene of Mouse and the heat shock promoter of Drosophila melanogaster (Sinclair et al., 1985, J. Mol. Cell. Biol. 5:3208).

SUMMARY OF THE INVENTION

In general the invention relates to the regulation of genes in eucaryotic cells using proteins or peptides derived from procaryotic cells. These proteins can bind to DNA upstream from or within the gene in the eucaryotic cell, and thus either turn gene expression on or off.

In general the invention features, in one aspect, the introduction of a procaryotic peptide into a eucaryotic cell such that the procaryotic peptide will effect the regulation of one or more genes in the eucaryotic cell. The procaryotic peptide is preferably able to bind to a specific DNA sequence and thence either turn on or turn off expression of a nearby eucaryotic gene. Most preferably the peptide binds to a DNA sequence found in procaryotic cells and not eucaryotic cells, which can be inserted into the eucaryotic cell near to the eucaryotic gene(s), the expression of which is (are) to be controlled. The procaryotic peptide is introduced into the eucaryotic cell by standard methodology. Preferably the peptide is encoded by a cloned gene which can be inserted into the eucaryotic cell on a plasmid or phage vector, or may be integrated into a chromosome. The expression of the peptide itself is preferably regulated by a promoter region so that the expression of the gene can be controlled by standard techniques, such as thermal inactivation (e.g. the Lambda $P_R$ promoter, under the control of the lambda cI$^{ts}$ gene); chemical stimulation or repression (e.g. the lacZ promoter under the control of isopropyl-$\beta$-d-thio-galactopyransoside IPTG); or stimulation or repression by a product of the same or another gene (e.g. the lexA promoter the under control of the lexA gene product).

In a second aspect the invention features the introduction of a second peptide, derived from a procaryotic cell, which is also able to bind to a specific DNA sequence. The specific sequence may be the same as or different to the one referred to above. Preferably the first peptide (above) is a repressor peptide and the second peptide is an activator so that by regulating the expression of each peptide one or more eucaryotic genes, which comprise the specific DNA sequence(s), may be regulated.

In a third aspect of the invention a procaryotic protein is produced in a eucaryotic cell as part of a hybrid protein. The hybrid protein is able to bind to a specific DNA sequence and to effect the expression of a nearby eucaryotic gene. Preferably the other part of the hybrid protein is a eucaryotic protein which effects the regulation of eucaryotic genes. Most preferably the hybrid protein activates the expression of a eucaryotic gene. The procaryotic protein part of the hybrid protein preferably dictates the specificity of binding of the hybrid protein, whilst the eucaryotic part dictates the effect of the hybrid protein on nearby eucaryotic genes. Such a hybrid protein is preferably encoded by a hybrid gene.

The advantages of the invention are that eucaryotic gene products can be specifically regulated within a eucaryotic system to produce active proteins when desired, without compromising the growth of the eucaryotic cell until expression of the gene is turned on. These constructions can be used in any desired eucaryotic cell system and with any eucaryotic protein product. The procaryotic peptide may be taken from any well-characterized system.

Other features and advantages of the invention will be apparent from the following description of the preferred embodiments and from the claims.

DESCRIPTION OF THE PREFERRED EMBODIMENTS

The drawings will first briefly be described.

Any cloned eucaryotic gene, the expression of which it is desired to regulate, may be used in the invention. Such eucaryotic genes encode a protein from their structural gene(s) and may comprise one or more introns. The gene may be borne on any vector or integrated into a chromosome and is generally under the control of its natural promoter. Such promoters, recognized by eucaryotic polymerases, for example, RNA polymerase II of the yeast Saccharomyces cerevisiae, contain at least two essential elements: a stretch of DNA containing a sequence homologous to TATA, and an upstream activator sequence (UAS) (Guarente et al. 1984 Cell 36:799). For example, synthesis of GAL1 mRNA, which begins 80 nucleotides downstream of the TATA region of the GAL1 promoter, depends on a sequence called $UAS_G$ located about 250 nucleotides upstream of the TATA region (Laemmli et al. 1970 Nature 227:680, FIG. 1). $UAS_G$ function has been localized to a 75-nucleotide sequence, and, more recently, to a 15-base pair (bp) sequence with approximate 2-fold rotational symmetry. The GAL4 gene product is thought to bind to this sequence in the presence of galactose to activate transcription downstream. When it is placed in front of the TATA region of CYC1, $UAS_G$ activates transcription from the hybrid promoter and renders this transcription inducible by galactose (Guarente et al., 1982 Proc. Natl. Acad. Sci. U.S. 79:7410). The distance between $UAS_G$ and a TATA region is not critical, and the effect of $UAS_G$ is still measurable even when it is located 500 nucleotides upstream of a TATA region. In these respects, $UAS_G$ shares properties with the transcriptional enhancer sequences found in higher eucaryotes.

In order to regulate the expression of eucaryotic genes a specific DNA sequence is introduced into the gene such that it may be regulated by a peptide, from a procaryotic cell, capable of specifically binding to the specific DNA sequence. Any procaryotic peptide which is known to regulate expression in procaryotic cells is suitable, the only requirement being that the specific DNA sequence to which it binds has been cloned or that a synthetic sequence is available. It is preferable to have a clone of the gene encoding the procaryotic peptide and even more preferable to have the expression of the gene under the control of a well known promoter so that the expression of the procaryotic peptide may be regulated. By regulating expression of the procaryotic peptide the expression of the eucaryotic gene, comprising the specific DNA sequence, may also be regulated. Generally such specific DNA sequences are termed operators or promoters.

Operators present in procaryotic cells have been extensively characterized in vivo and in vitro and can be readily manipulated to place them in any position upstream from or within a gene by standard techniques. Such operators comprise promoter regions and regions which specifically bind proteins such as activators, repressors, and ribosome subunits. One example is the operator region of the lexA gene of *Escherichia coli* to which the LexA peptide binds. Other examples include the operator regions of the lactose and tryptophan operators, to which the repressor proteins encoded by the lacI and trpR genes of *E. coli* bind, the operator region of the Lambda $P_R$ gene to which the repressor protein encoded by the Lambda cI gene binds, or other commonly used repressor proteins such as the gal repressor of *E. coli* and the repressor proteins from phages related to Lambda.

EXAMPLE 1

In this example the expression of the eucaryotic gene GAL4, from yeast, is regulated by the cloned procaryotic peptide LexA, encoded by the lexA gene of *E. coli*.

pRB500 is a plasmid which directs the synthesis of LexA protein and was made by inserting a 1,000-nucleotide HindIII-HindIII piece from pRB480, which contained DNA from 62 bases upstream to ~200 nucleotides downstream of lexA, into the HindIII site of pAAH5 (Brent et al., 1984, Nature 312:612). pAAH5 is a plasmid which carries the LEU2 gene, a $2\mu$ origin of replication, and several hundred nucleotides of DNA from around the ADH1 (ADCI) promoter. The ADH1 fragment ends 11 nucleotides upstream of the ATG that would begin the ADH1 structural gene. At this site a HindIII linker has been inserted.

Figure 1:
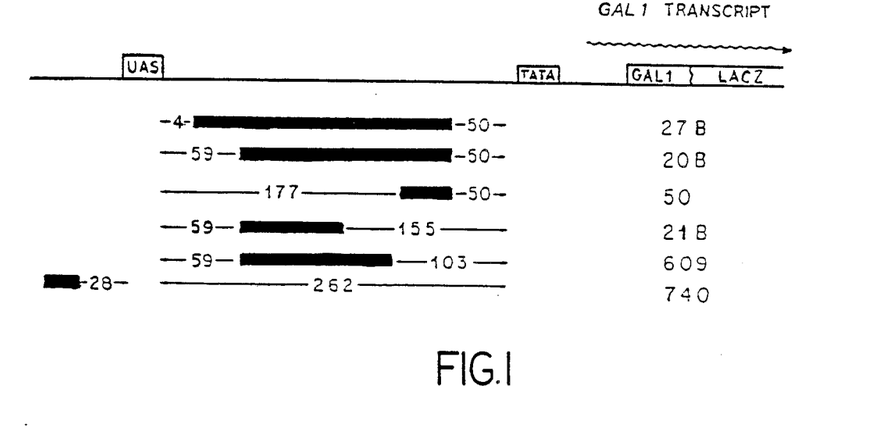
FIG. 1 is a diagrammatic representation of derivatives of the GAL1 promoter of Yeast (Saccharomyces cerevisiae).

Referring to FIG. 1, one or more synthetic lexA operators of the sequence:

TCGAGTACTGTATGTACATACAGTAC
CATGACATACATGTATGTCATGAGCT were inserted directly into XhoI cut GAL1 promoter derivatives (shown in FIG. 1) using standard plasmid construction techniques. The distance from the XhoI site to the TATA region and to the upstream activator sequence for various promoter derivatives is given in number of nucleotides. The $UAS_G$ region contains two homologous 15-nucleotide regions of approximate 2-fold rotational symmetry separated by three nucleotides (one of which is sufficient for $UAS_G$ function). When defined in this way, there are 262 nucleotides between $UAS_G$ and the first base of the TATA sequence. Numbering of the GAL1 derivatives is from the centre of the XhoI recognition sequence to the closest base in the upstream activator sequence, and to the first T of the GAL1 TATA sequence. The mature GAL1 transcript begins 85 nucleotides downstream o of this T, and the GAL1 coding sequence begins 60 nucleotides farther downstream. The extent of GAL1 promoter deleted in each derivative is shown by a dark bar. 36 nucleotides are deleted in the mutant 740. Mutants 609, 740, 20B and 27B were constructed as described in West, et al. (1984, Molec. Cell Biol. 4:2467); 50 and 21B were also constructed as described in West et al. (Idem).

The GAL1 promoter derivatives are carried on plasmids with a replicator and a selectable marker (URA3). Using standard techniques, the GAL1 structural gene was fused in each case to a lacZ gene (of *E. coli*) so that the β-galactosidase level in a plasmid-carrying cell was a measure of GAL1 transcription (Need details or a Ref. as described in West et al., supra.

Bacterial strains, with or without plasmids comprising the lexA gene and/or the lexA promoter linked to GAL1, were grown in LB medium which contained, when appropriate, tetracycline at a concentration of 15ug/ml, carbenecillin at 60 ug/ml, and IPTG at $5\times10^{-4}$M. Yeast, with or without plasmids, were grown on YEPD medium, or, when they contained plasmids, on minimal medium containing either glucose 2% weight/volume ("glucose medium") or galactose at the same concentration ("galactose medium") but lacking either leucine or uracil or both (Sherman et al., 1983 Methods in Yeast Genetics. Cold Spring Harbor, NY, Cold Spring Harbor Laboratory). Yeast were made competent by treatment with lithium acetate (Ito et al., 1983 J. Bacteriol 53:163). The amount of beta-galactosidase in liquid cultures of *E. coli* was measured according to Miller (1972 Experiments in Molecular genetics, Cold Spring Harbor, NY, Cold Spring Harbor Laboratory) and determined for *S. cerevisiae*, in liquid culture and from the degree of blue color on indicator plates containing 5-bromo-4-chloro-3-indolyl-βD-galactopyranoside, (Brent et al., Idem). In strain DBY745, results of liquid assays were consistent from day to day; in contrast, due to a tendency of cells in cultures of the gal4⁻ strain SHC22C to form clumps on some days but not on others, liquid assays had to be repeated many times to generate reliable data. For all strains used, estimation of beta-galactosidase activity from color on indicator plates was consistent from day to day.

The effect of LexA protein on the lexA operator derivative plasmids was shown by transforming yeast strain D8Y 745 with two types of plasmids having two different selectable markers. One plasmid directed the synthesis of LexA protein and carried the LEU2 marker (pRB500, the control was pAAH5 which lacks the lexA gene). Another plasmid contained a derivative of the yeast GAL1 promoter with a lexA operator site and carried the URA3 marker. Transformed yeast were isolated and propagated on medium that selected for cells bearing both plasmids (i.e., for URA+, LEU+- colonies). The amount of transcription from the GAL1 promoter was measured after cultures of doubly transformed cells had been grown on galactose-containing medium for at least five generations. The derivatives of the GAL1 promoter in which lexA operators were installed are shown in FIG. 1.

TABLE 1

LexA protein repression of GAL1 promoter with lexA operators

|  | Control plasmid | lexA plasmid |
| --- | --- | --- |
| 20B | 5,000 | 5,000 |
| +1 op | 2,500 | 350 |
| +2 op | 2,500 | 250 |
| 27B | 1,800 | 1,800 |
| +1 op | 1,000 | 150 |
| 50 | 5,000 | 5,000 |
| +1 op | 2,500 | 600 |
| +2 op | 2,400 | 500 |
| 21B | 5,000 | 5,000 |
| +1 op | 2,500 | 400 |
| +2 op | 2,300 | 250 |
| 609 | 5,000 | 5,000 |
| +1 op | 3,100 | 400 |
| 740 | 5,000 | 5,000 |
| +1 op - | 5,000 | 5,000 |

Derivatives of the GAL1 promoter containing lexA operators between the upstream activator sequence and the TATA region (derivatives 27B, 20B, 50, 21B and 609; FIG. 1) were repressed 4–10-told by LexA protein (Table 1; +1 op- one synthetic operator, +2 op- two synthetic operators). All GAL1 promoter derivatives containing two lexA operators were repressed more efficiently than corresponding derivatives that contained only a single operator. No repression was observed when the operator was installed upstream of the $UAS_G$ (in GAL1, derivative 740; see FIG. 1). In the absence of LexA protein, lexA operators at certain sites in the GAL1 promoter slightly diminished transcription (Table 1). This effect may be related to the slight homology between the lexA operator and sequences implicated in yeast transcription termination.

The presence of LexA protein in transformed yeast cells was demonstrated as follows: Yeast strain DBY745 (α adel-100 leu2-3 leu2-112 ura3-52) was transformed with pAAH5 or pRB500, using the lithium acetate technique. Extracts were produced by growing the yeast cells in glucose minimal medium without leucine (Abraham et al. 1984 J. Molec. Biol. 176:107) to a density of $2 \times 10^7$ ml$^{-1}$. 2 ml of this culture was concentrated by centrifugation, resuspended in 0.2 ml Laemmli sample buffer, (Laemmli, 1970 Nature 227:680) and lysed by grinding with glass beads (Bennetzen et al., 1983 J. Biol. Chem. 258:1165). 0.05 ml of each extract was run on a 12% polyacrylamide/SDS gel (Laemmli, Idem). Proteins in the gel were transferred electrophoretically to a nitrocellulose membrane, the membrane probed with anti-LexA protein antibody followed by $^{125}$I-protein A from Staphylococcus aureus (Silver et al. Proc. Nat. Acad. Sci. U.S. 81, in press). The membrane was washed and exposed to XAR-5 film for 24 hours. LexA protein was present in yeast cells comprising pRB500 but not pAAH5. From immunoprecipitation experiments and from strained gels, it could be estimated that LexA protein constituted between 0.02% and 0.1% of the total soluble protein in cells transformed with pRB500 grown in glucose.

In order to confirm that the apparent lexA-mediated repression of operator-containing GAL1 promoters was not caused by variation in plasmid copy number, nonreplicating derivatives of two lexA-repressible GAL1 plasmids were constructed and their integration directed into a yeast chromosome (Orr-Weaver et al. 1981 Proc. Nat. Acad. U.S. 78:6348) as follows: Plasmid 118 (20B+2 lexA operators) was partially digested with EcoRI, ligated, and the ligation mixture cut with XbaI to linearize plasmids that retained the EcoRI fragment from 118 containing the 2μ origin. The ligation mixture was used to transform E. coli strain JM101 (Groneborn et al. 1978 Nature 272:375), which lacks a functional lacZ gene. 427, a derivative of 118 that lacks the EcoRI fragment containing the replication origin, was isolated from a lacZ+, Amp$^R$ colony. 427 was cut in its URA3 gene with ApaI and lithium acetate-treated yeast strain DBY745 was transformed with the cut plasmid DNA. Six URA+ transformants arising from this construction were checked to see that the URA marker was not lost after growth for 40 generations on nonselective medium, and that GAL1 promoter transcription in these strains was normally inducible if the yeast were grown on medium containing galactose. These six strains were made competent with lithium acetate, transformed to LEU+ with a plasmid directing the synthesis of LexA protein, pRB500, or with its parent plasmid, pAAH5. β-Galactosidase in these strains was assayed, in liquid and on indicator plates. There was no variation in GAL1 transcription among the six strains when grown on galactose, glucose, and galactose with GAL1 transcription repressed by LexA protein. Thus repression by LexA protein was as efficient, but no more efficient, that the repression observed when the operator-containing GAL1 promoter was present in many copies on a plasmid.

The preceding data provide genetic evidence that a bacterial repressor protein manufactured in the yeast cytoplasm can enter the yeast nucleus, recognize its operator and repress transcription from a yeast promoter. Immunofluorescence tests show that LexA protein is localized to the nucleus in a minority of cells in a population that produce it. In most members of the population, fluorescence is uniformly spread throughout the cytoplasm and it is likely that LexA protein passively enters the nucleus. This behaviour is in contrast to the strictly nuclear localization of regulatory proteins native to yeast, which are thought to have a distinctive stretch of amino acids causing them to enter and remain in the nucleus (Hall et al. 1984 Cell 36:1057). Uniform cellular distribution of LexA protein should be sufficient to repress operator-containing GAL1 promoters. If LexA protein constitutes 0.025% of the total protein in cells grown on galactose, and if it is evenly distributed throughout the cell, there should be about 750 LexA molecules in the nucleus. As the volumes of

*E. coli* and a yeast nucleus are about the same, nuclear LexA protein concentration is probably equivalent to the concentration found in a single *E. coli*, which contains 100–1,000 molecules of LexA protein. We have shown here that the affinity of the synthetic operator for LexA protein is at least as high as that found for naturally occuring lexA operators. Therefore, 100–1,000 molecules of LexA per nucleus should be sufficient to occupy the operator.

EXAMPLE 2

In this and the following example a hybrid protein of LexA and GAL4 was constructed and shown to regulate expression of genes in both procaryotic and eucaryotic systems.

Figure 3:
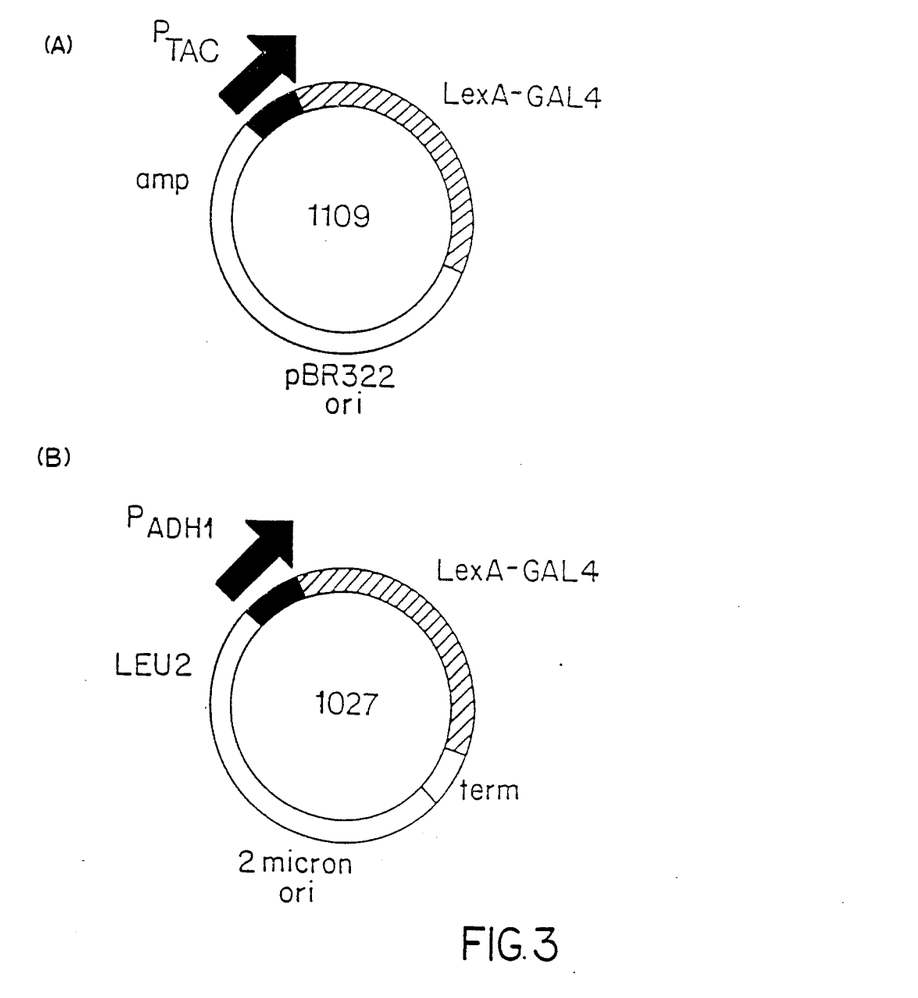
FIG. 3 is a schematic representation of plasmids encoding a hybrid procaryotic/eucaryotic protein.

Referring to FIG. 3, plasmid 1109, which directs the synthesis of LexA-GAL4 in *E. coli*, was constructed from three DNA fragments. In this construction, a PstI-XmnI piece was isolated from pRB451, a tac promoter derivative of pRB191 (Brent et al., 1981 Proc. Nat. Acad. Sci. 78:4204). This piece of DNA contained the tac promoter, a hybrid ribosome binding site, and lexA DNA from codon 1 to within codon 87. A plasmid (Silver et al. 1984, Proc. Nat. Acad. Sci. 81:595), containing the *S. cerevisiae* GAL4 gene was cut with XhoI, the XhoI ends rendered flush by treatment with the Klenow fragment of DNA polymerase I, then cut with HindIII to liberate a fragment of DNA that encoded the C-terminus of GAL4, extending from the filled-in XhoI site within codon 74 (Laughon et al., 1984 Mol. Cell Biol. 4:260) to about 250 nucleotides beyond the termination codon after amino acid 881. These two pieces were inserted into a PstI-HindIII backbone fragment of pBR322 (Bolivar et al., 1977 Gene 2:95).

Figure 2:
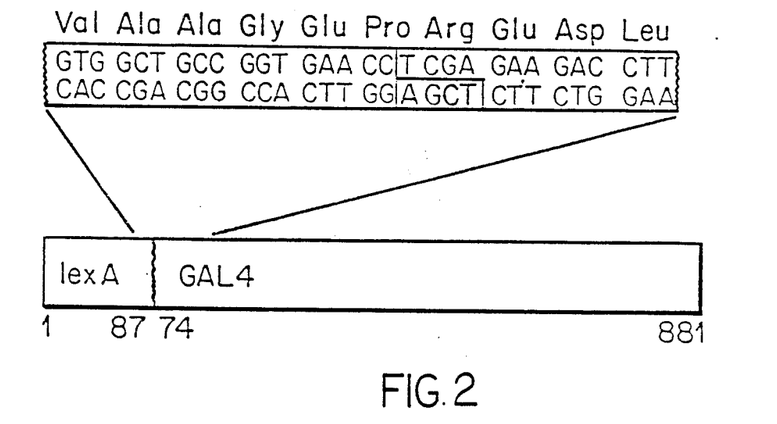
FIG. 2 is the sequence of the lexA-GAL4 fusion junction.

Plasmid 1027 (FIG. 3b), which directs the synthesis of LexA-GAL4 in *S. cerevisiae*, was constructed in two steps. In the first the HindIII-XmnI fragment from pRB500 was isolated. This fragment contained DNA from immediately upstream of the lexA coding sequence to within codon 87. This fragment was inserted, and the same GAL4 fragment used in constructing 1109 above, into plasmid pi$^4$-8, constructed from pBR322 restricted with HindIII and EcoRI, filled in using Klenow fragment and ligated to the 750bp HpaII-Sau3IIIA Klenow treated fragment of phage 434, which includes the cI repressor gene and rightward promotor), that confers resistance to tetracycline when HindIII-ended fragments are inserted into it. This ligation created plasmid 1002, which contained the lexA-GAL4 hybrid gene flanked by HindIII sites. The HindIII-ended lexA-GAL4 fragment from 1002 was inserted into pAAH5, a plasmid that contains the ADH1 promoter, the LEU2 selectable marker, and the 2 micron replicator, to create plasmid 1027. Like all plasmids from this construction that contained the gene encoding LexA-GAL4 in the correct orientation, purified 1027 transformed JM101% of the frequency expected from the amount of DNA used, and most transformed cells grew slowly. About 10% of the JM101 cells transformed to carbenicillin resistance from a preparation of 1027 grew quickly and proved to contain plasmids that carried deletions or portions of the gene encoding LexA-GAL4. The sequence of LexA-GAL4 fusion junction is shown in FIG. 2. The lexA coding sequence extending to the XmnI site within the hinge region (vertical line), was abutted to a filled-in XhoI site in GAL4, as described above. Bases of the filled-in site are shown in boldface. This ligation recreated the XhoI site. The amino acid sequence of the protein near the fusion junction is shown above the line. For assay of LexA-GAL4 activity, cells were first transformed with 1027 or another LEU2$^+$ plasmid. As determined by their ability to activate beta-galactosidase production from a plasmid that contained a LexA operator near a LacZ fusion gene, about 90% of the 1027 transformants produced LexA-GAL4.

In order to demonstrate that in *E. coli*, LexA-GAL4 recognizes lexA operators the fact that LexA represses transcription of its own gene was exploited (Brent et al., 1980 Idem). In the bacterial strain used in this procedure, F$^1$ (lacI$^{q1}$ lacZ::Tn10)/lexA (def)Δ(lac-pro) arg ile val thi A str$^R$, which was constructed by standard techniques and lysogenized with RB230, an imm$^{21}$ phage that contains the lexA promoter fused to an operon that contains trpA and lacZ, similar to RB200 (Brent et al., 1980, Idem), the lacZ gene was fused to the lexA promoter, so that the amount of beta-galactosidase in the strain was a measure of transcription from that promoter. The strain also carried a mutation that inactivated the chromosomal lexA gene. It was transformed separately with the plasmids shown in Table 2, which encoded regulatory proteins under the control of the lac or tac promoters. In these procedures, IPTG was added to the culture medium to inactivate lac repressor and induce synthesis of the respective proteins. Cells were grown to a density of $1 \times 10^6$ cells / ml in LB medium that contained 60ug/ml carbenicillin. At this point IPTG was added to the culture to a concentration of $5 \times 10^{-4}$M. Growth was resumed for four hours and beta-galactosidase was assayed as described above, with the results shown in Table 2. Numbers refer to units of beta-galactosidase activity in different cultures. The data demonstrate that LexA-GAL4 repressed transcription from the lexA promoter by 16 fold.

TABLE 2

| plasmid | regulatory protein produced | units of B-gal |
|---|---|---|
| pBR322 | none | 2000 |
| pKB280 | lambda repressor | 1800 |
| PRB451 | LexA | 120 |
| 1109 | LexA-GAL4 | 140 |

EXAMPLE 3

To demonstrate the effect of LexA-GAL4 protein in yeast, yeast were transformed with the plasmids, described in example 2, that direct the synthesis of LexA-GAL4 (FIG. 3), and separately transformed with a plasmid that directs synthesis of native LexA (pRB500). These strains were additionally transformed with plasmids that carried the constructs shown in FIG. 4.

Figure 4:
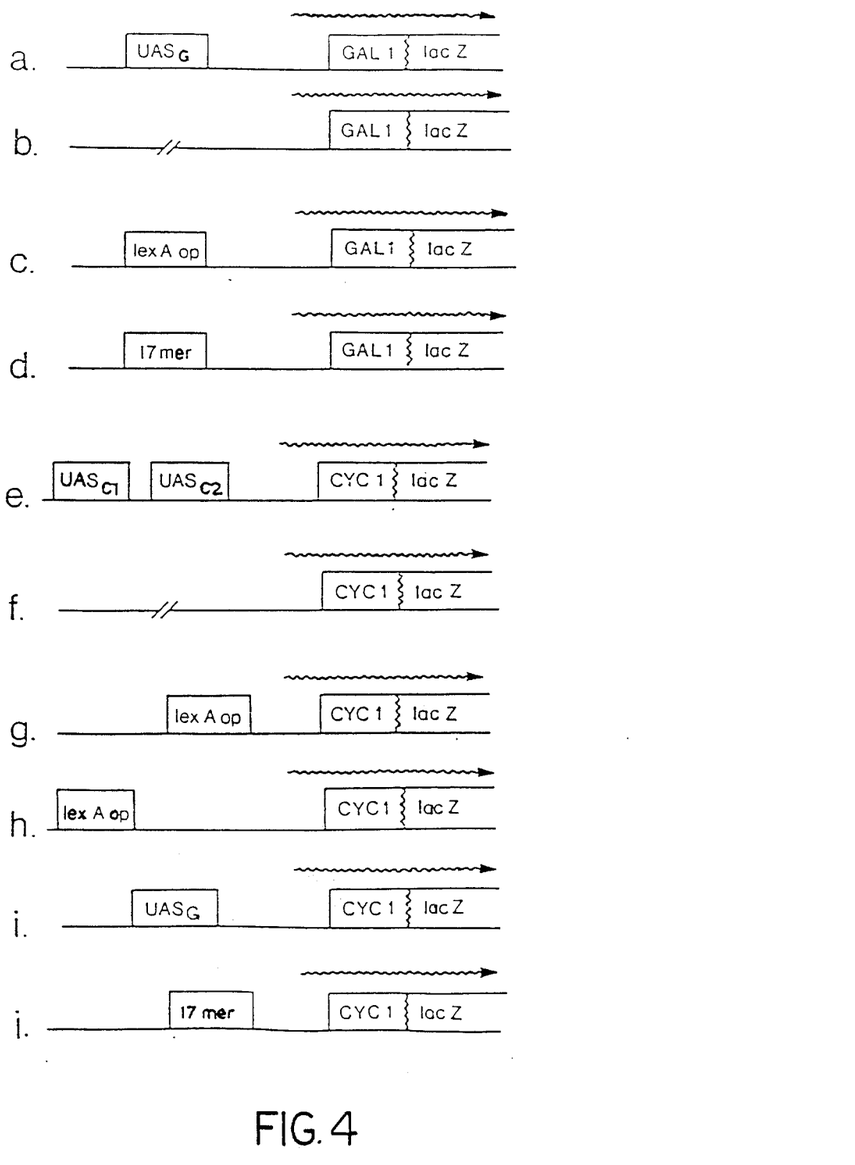
FIG. 4 is a schematic representation of DNA constructions containing the lexA operator sequence in various positions, and relevant control constructions. The position of the relevant element is given as number of nucleotides from the GAL4 or CYC1 start codons. (a) LR1Δ20B, 128 nucleotides; (b) LR1Δ1, lacks an upstream element; (c) 1145, 167 nucleotides; (d) pSV15, 128 nucleotides; (e) pLG669-Z, about 190 nucleotides; (f) pLG670Z, lacks an upstream element; (g) 1155, 178 nucleotides; (h) 1057, 577 nucleotides; (i) pLGSD5, about 190 nucleotides; (j) pSV14, 178 nucleotides.

Referring to FIG. 4, these plasmids carry part of the GAL1 or CYC1 gene fused to lacZ. Upstream of the fusion gene the plasmids contain one of the following: UAS$_G$, 17-mer (the 17bp near-consensus GAL4 site of action, Gininger et al., 1985 Cell 40:767), UAS$_{C1}$, and UAS$_{C2}$ (Guarente et al., 1984 Proc. Nat. Acad. Sci. 81:7860), a lexA operator, or none of these elements. All plasmids carry the URA3$^+$ gene and, a 2μ replicator. LR1Δ20B, which contains UAS$_G$ and the GAL1 gene fused to lacZ, and LR1Δ1, which does not contain UAS$_G$, have been described (West et al., 1984 Mol. Cell Biol. 4:2467). 1155 was made from LRΔ1 by inserting a single synthetic consensus lexA operator (Brent et al., 1984, Nature 312:612) into the Xho1 site of the plasmid, 167 nucleotides from the primary transcription start site. pSV15 is a derivative of LR1Δ20B in which UAS$_G$ has been deleted and replaced with a DNA fragment, 128 nucleotides upstream of the primary GAL1 transcription start site, that contains the "17-mer". pLG669-Z, which carries UAS$_{C2}$ upstream of a CYC1-lacZ fusion gene, and pLGSD5, which carries UAS$_G$ upstream of the CYC1-lacZ gene, have been described (Guarente et al., 1981 Proc. Nat. Acad. Sci. 78:2199; Guarente et al., 1982 Proc. Nat. Acad. Sci. 79:7410). pLG670Z is a derivative of pLG669-Z from which the Xho1-Xho1 fragment that contains the upstream activation sites has been deleted. 1057 and 1155 were constructed from pLG670Z by inserting a single lexA operator at the Xho1site or the Sal1 site, 178 and 577 nucleotides upstream of the most upstream CYC1 transcription start site, respectively. pSV14 is a derivative of pLG670Z in which a fragment of DNA that contains the 17-mer has been inserted at the Xho1 site 178 nucleotides upstream of the CYC1-lacZ fusion gene. HZ18 was described by Teem et al., (1983 Proc. Nat. Acad. Sci. 80:4403). It contains a Sal1 site in the RP51 intron about 160 nucleotides downstream from the most upstream CYC1 transcription start site. 1146 was constructed from HZ18 by inserting a lexA operators into the Sal1 site. The amount of transcription of the lacZ fusion genes, was measured as the amount of beta-galactosidase activity in cultures of these doubly transformed cells.

LexA-GAL4 stimulated production of beta-galactosidase directed by the CYC1-lacZ fusion gene if and only if the plasmid contained a lexA operator, as shown in Table 3. (In the table, the letters in parenthesis refer to the construction diagrammed in FIG. 4.)

TABLE 3

LexA-GAL4 Trascription of a CYC-Fusion Gene

| Growth Medium | Upstream Element | Regulatory Protein | |
|---|---|---|---|
| | | LexA | LexA-GAL4 |
| Galactose | no UAS (f) | <1 | <1 |
| | lexA op at −178 (g) | <1 | 590 |
| | lexA op at −577 (h) | <1 | 420 |
| | UAS$_{C1}$ and UAS$_{C2}$ (e) | 550 | 500 |
| | UAS$_G$ (i) | 950 | 950 |
| | 17-mer (j) | 600 | 620 |
| Glucose | no UAS (f) | <1 | <1 |
| | lexA op at −178 (g) | <1 | 210 |
| | lexA op at −577 (h) | <1 | 140 |
| | UAS$_{C1}$ and UAS$_{C2}$ (e) | 180 | 160 |
| | UAS$_G$ (i) | <1 | <1 |
| | 17-mer (j) | <1 | <1 |

When the lexA operator is located 577 nucleotides upstream of the nearest CYC1 transcription start site, beta-galactosidase production was two thirds that obtained when the lexA operator was positioned 178 nucleotides upstream. Compared to the amount obtained when cells were grown in medium that contained galactose as the only carbon source, the amount of beta-galactosidase directed by LexA-GAL4 in cells grown in glucose medium was diminished by about a factor of three. Native LexA did not stimulate beta-galactosidase production from these plasmids.

LexA-GAL4 also stimulated production of beta-galactosidase from a plasmid that contained the GAL1-lacZ fusion gene if and only if the plasmid contained a lexA operator. Growth of cells in glucose medium decreased that stimulation by about half. Native LexA did not stimulate beta-galactosidase production.

The above procedures were performed in a GAL4+ host. *Similar procedures were performed in two other strains, one of which carried a gal4 point mutation, the other a gal4 deletion.* In these strains, LexA-GAL4 stimulated beta-galactosidase production from the CYC1-lacZ plasmids if and only if they contained a lexA operator. In particular, LexA-GAL4 did not stimulate beta-galactosidase production from plasmids that contained UAS$_G$ but no lexA operator, nor from an integrated GAL1-lacZ fusion gene, nor did it complement the gal4− strains' inability to grow on galactose medium. As above, LexA-GAL4 directed synthesis of less beta-galactosidase production from the CYC1-lacZ fusion gene when the lexA operator was located 577 nucleotides upstream of the nearest transcription start site than when it was 178 nucleotides upstream.

Figure 5:
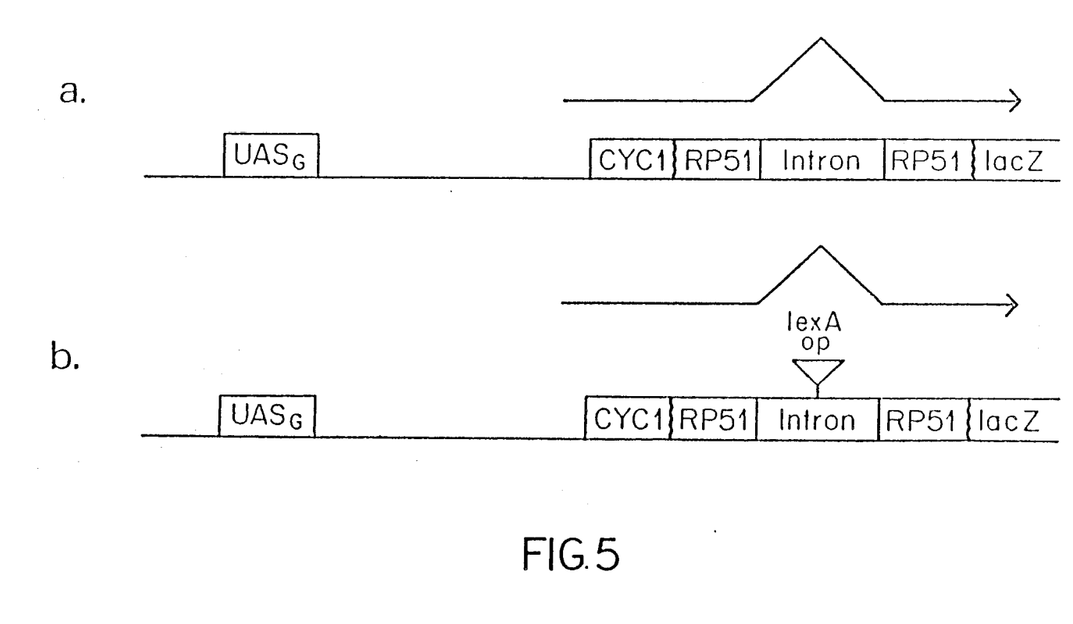
FIG. 5 is a schematic representation of DNA constructions used to demonstrate downstream activation.

In order to test whether LexA-GAL4 could activate transcription from a site downstream of the normal transcription start, a lexA operator was inserted into the intron of a spliced yeast gene, downstream of the normal transcription start site. The lexA operator was inserted into the plasmid diagrammed in FIG. 5 (Teem et al., 1983 Idem, Guarente et al., 1984 Cell 36:503). The arrow represents a transcript when transcription is activated by UAS$_G$ upstream. FIG. 5(a) shows the plasmid HZ18 (Teem et al., Idem), and FIG. 5(b) a derivative of HZ18, 1146, which bears a lexA operator in the RP51 intron. Plasmid HZ18 contains UAS$_G$ upstream of the CYC1 coding sequence, which is fused to a fragment containing a portion of RP51, a gene whose transcript is spliced. The RP51 fragment contains part of the first exon, the intron, and part of the second exon. The second exon of RP51 is fused to lacZ. Insertion of a lexA operator into the intron allows determination of whether LexA-GAL4 activates transcription when bound downstream of the transcription startpoint, by measuring beta-galactosidase produced by the plasmid.

LexA-GAL4 stimulated production of beta-galactosidase if and only if the RP51 intron contained a lexA operator. No beta-galactosidase was produced if LexA was present instead of LexA-GAL4. This test was done in a gal4− strain, to eliminate upstream activation by UAS$_G$. Beta-galactosidase activity in this test was about 4% of the level observed in a GAL4+ strain when transcription was activated from UAS$_G$ upstream.

EXAMPLE 4

In order to demonstrate the broad applicability of the invention a second hybrid protein, composed of LexA and a positive regulator of amino acid biosynthesis encoded by GCN4, was constructed (Lucchini et al. 1984 Mol. Cell Biol. 4:1326, Driscoll-Penn et al., 1983 Proc. Nat. Acad. Sci. 80:2704) (How?). LexA-GCN4 activates transcription from the lexA operator containing constructions used in the example above.

Plasmids pRB500 and 1027, in *E. coli* strain JM101, are being deposited with the American Type Culture Collection (ATCC) on Aug. 22, 1988 and assigned numbers 67758, and 67759, respectively.

We claim:

1. A method of regulating the expression of a gene in a eucaryotic cell, said method comprising:
    providing in said eucaryotic cell, a peptide, derived from or substantially similar to a peptide of a procaryotic cell able to bind to DNA upstream from or within said gene, the amount of said peptide being sufficient to bind to said gene and thereby control expression of said gene.
2. The method of claim 1 wherein said peptide is substantially similar to a peptide of *E. coli*.

3. The method of claim 2 wherein said peptide is the product of the lexA, lacI, trpR, or Lambda cI genes.

4. The method of claim 2 wherein said peptide is a fusion peptide.

5. The method of claim 4 wherein said fusion peptide is the product of a gene fusion.

6. The method of claim 5 wherein said gene fusion comprises the fusion of GAL4 with the lexA, lacI, trpR, or Lambda cI repressor genes.

7. The method of claim 1 wherein said peptide is encoded by a plasmid borne gene.

8. The method of claim 1 wherein said peptide is present in the cytoplasm of said eucaryotic cell.

9. The method of claim 1 wherein said peptide is encoded by a gene integrated into a chromosome of said eucaryotic cell.

10. The method of claim 1 wherein said method further comprises regulating the expression of said peptide and thence the expression of said gene in said eucaryotic cell.

11. The method of claim 10 wherein said regulation of said peptide is thermal, chemical, or by the product of another gene within said eucaryotic cell.

12. The method of claim 1 wherein said gene in said eucaryotic cell comprises a procaryotic gene operator sequence.

13. The method of claim 12 wherein said operator is the operator sequence to which the product of the lexA, lacI, trpR, or Lambda cI gene binds.

14. The method of claim 1 wherein said eucaryotic cell comprises a second peptide, derived from or substantially similar to a second peptide of a procaryotic cell able to bind to DNA upstream from or within said cell, and thereby control expression of said gene.

15. The method of claim 14 wherein said peptide is a repressor peptide and said second peptide is an activator peptide.

16. The method of claim 15 wherein said peptide and said second peptide compete for a region on said DNA upstream from or within said gene.

17. The method of claim 16 wherein said peptide or said second peptide may be inactivated and thereby allow said remaining peptide or said remaining second peptide to bind to said DNA upstream from or within said gene.

18. The method of claim 17 wherein said inactivation is thermal, chemical, or by the product of another gene within said eucaryotic cell.

19. A hybrid gene comprising DNA encoding a specific DNA binding procaryotic peptide and DNA encoding a gene activating eucaryotic peptide, said gene activating peptide being effective to enhance transcription of adjacent DNA.

20. The hybrid gene of claim 19 wherein said specific binding peptide is a segment of a first protein derived from a procaryotic cell.

21. The hybrid gene of claim 20 wherein said first protein represses the transcription of a gene within said procaryotic cell.

22. The hybrid gene of claim 21 wherein said procaryotic cell is *E. coli*.

23. The hybrid gene of claim 22 wherein said first protein is the product of the lexA, lacI, trpR, or Lambda cI genes.

24. The hybrid gene of claim 19 wherein said gene activating peptide is a segment of a second protein derived from a eucaryotic protein.

25. The hybrid gene of claim 24 wherein said second protein activates the transcription of a gene in said eucaryotic cell.

26. The hybrid gene of claim 25 wherein said eucaryotic cell is yeast.

27. The hybrid gene of claim 26 wherein said gene activating peptide is the product of the GAL4 gene.

28. A eucaryotic cell comprising a peptide derived from or substantially similar to a peptide of a procaryotic cell able to bind to DNA upstream from or within said gene, and thereby control expression of said gene.

29. A eucaryotic cell as claimed in claim 28 in which said peptide represses the transcription of a gene in said eucaryotic cell.

30. The eucaryotic cell of claim 29 wherein said eucaryotic cell is yeast.

31. The eucaryotic cell of claim 30 wherein said procaryotic protein is derived from or substantially similar to a protein in *E. coli*.

32. The eucaryotic cell of claim 31 wherein said procaryotic protein is the product of the lexA, lacI, trpR, or Lambda cI genes.

* * * * *

UNITED STATES PATENT AND TRADEMARK OFFICE
CERTIFICATE OF CORRECTION

PATENT NO. : 4,833,080

DATED : May 23, 1989

INVENTOR(S) : Roger Brent et al.

It is certified that error appears in the above-identified patent and that said Letters Patent is hereby corrected as shown below:

Column 1, line 9, "in vivo" should be --*in vivo*-- (italicized).

Column 3, line 43, "in vivo and in vitro" should be --*in vivo* and *in vitro*-- (italicized).

Column 4, line 29, delete "o" after "downstream".

Column 4, line 42, delete "(Need details or a Ref."

Column 4, line 43, "supra" should be --*supra*-- (italicized).

Column 4, line 49, "M" should be --*M*--.

Column 4, line 64, "indolyl-βD-galac-" should be --indolyl-β D-galac- --.

Column 5, line 15, "LEU$^{+-}$" should be --LEU$^{+}$--.

Column 7, line 56, "JM101?" should be --JM101 at 1%--.

Column 8, line 6, "LexA" should be --lexA--.

Column 8, line 31, "M" should be --*M*--.

UNITED STATES PATENT AND TRADEMARK OFFICE
CERTIFICATE OF CORRECTION

PATENT NO. : 4,833,080

DATED : May 23, 1989

INVENTOR(S) : Roger Brent et al

It is certified that error appears in the above-identified patent and that said Letters Patent is hereby corrected as shown below:

Column 9, lines 67-68, should be no change in font.

Signed and Sealed this

Twenty-third Day of January, 1990

Attest:

JEFFREY M. SAMUELS

*Attesting Officer*  *Acting Commissioner of Patents and Trademarks*